United States Patent [19]

von Gutfeld et al.

[11] Patent Number: 5,013,241
[45] Date of Patent: May 7, 1991

[54] ULTRASONIC JET DENTAL TOOL AND METHOD

[76] Inventors: Robert J. von Gutfeld, 600 W. 115th St., New York, N.Y. 10025; Nelly Ropper, 205 West End Ave., New York, N.Y. 10023

[21] Appl. No.: 409,042

[22] Filed: Sep. 18, 1989

[51] Int. Cl.⁵ .............................................. A61C 1/07
[52] U.S. Cl. ................................... 433/86; 128/62 A; 128/24 A
[58] Field of Search ......................... 433/86, 119, 216; 128/24 A, 62 A

[56] References Cited

U.S. PATENT DOCUMENTS

| | | | |
|---|---|---|---|
| 3,522,801 | 8/1970 | Robinson | 433/86 |
| 3,636,947 | 1/1972 | Balamuth | 128/24 A |
| 3,771,517 | 11/1973 | Radecki | 128/66 |
| 3,924,335 | 12/1975 | Balamuth et al. | 433/119 |
| 4,012,842 | 3/1977 | Vit | 433/216 |
| 4,071,956 | 2/1978 | Andress | 433/216 |
| 4,116,239 | 9/1978 | Ewen | 433/119 |
| 4,331,422 | 5/1982 | Heyman | 433/86 |

OTHER PUBLICATIONS

Instruction Manual—Dentsply/Cavitron—Prophy-Jet C-300, Dentsply International Inc., No. 3535 Rev. 5M 3/84.

*Primary Examiner*—Cary E. Stone

[57] ABSTRACT

A dental tool and method for removing plaque from teeth and for cleaning teeth, as well as for other applications, wherein ultrasonic energy is coupled into a liquid stream that impinges upon the teeth to be cleaned. The ultrasonic energy cleans the teeth and removes plaque, while the liquid stream provides a carrier for the ultrasonic energy and carries away any debris produced during plaque removal or cleaning. The jet stream is a very gentle one which does not cause harm to teeth or gums and can be used in the home as well as by professionals. No discomfort is caused through heating, scraping, or abrasive action.

28 Claims, 1 Drawing Sheet

ULTRASONIC JET DENTAL TOOL AND METHOD

FIELD OF THE INVENTION

This invention relates to a dental tool and method for preventing the build-up of plaque on teeth, and more particularly to a dental tool for this purpose which can be used at home or by the dentist and which directs a sonified liquid stream to the tooth to be cleaned, the sonic energy removing plaque on the tooth.

BACKGROUND ART

The build-up of plaque is a leading cause of periodontal disease, which is a common affliction affecting many people. At the present time only regular brushing and flossing are consiered safe as preventative measures to excessive build-up of plaque. However, these measures are not totally effective for individuals who are very prone to plaque build-up. Even with this type of regular dental care, many individuals require periodic surgery and deep cleaning to avoid excessive build-up of plaque.

In the art, dentists resort to various abrasive cleaning techniques to physically remove plaque. These techniques augment the use of cleaners having abrasives therein which are rubbed against teeth by the dentist using a drilling tool equipped with a cleaning wheel.

Commercially available instruments for cleaning teeth are known which provide a pulsed water stream to remove particles from teeth in order to prevent decay. A burst of water can drive particles from the teeth but may implant particles into the gums, causing problems. A high pressure water stream without chemical additives (e.g. sodium bicarbonate) will not remove plaque efficiently and can cause other harm to gums. Also, this technique may loosen the gums from around the teeth due to the force of the water stream. If pockets are present in cases of periontitis, food particles can be driven into the pockets causing absesses, etc.

In the art, it is also known to apply ultrasonic energy in periodontics. Several types of equipment are available for this purpose including the Cavitron Model 660, the Ultrason 880, and the Sonic Scaler. Generally, all of these ultrasonic units are characterized by the use of a solid (metal) tip to which ultrasonic energy is applied. The vibrating metal tip is used to contact a tooth in order to remove plaque therefrom. Because of the heat build-up inherent in such an operation, rinsing water and cooling flows are normally used. The probe vibration frequency is typically 25 KHz. The apparatus usually consists of an ultrasonic generator which provides a current to a coil wrapped around a magnetostrictive transducer coupled to a vibrating tip. The electrical energy from the generator is applied to the transducer which in turn converts the electrical energy into vibrations. These vibrations are transmitted to the tip that is used to contact the teeth.

This type of ultrasonic dental tool can create a very uncomfortable feeling in the patient due to the high intensity vibrations that bear upon the teeth to be cleaned. Nerve pain can be caused along with heat, so water or a cooling liquid is required to prevent tooth burning. In some of this equipment, high pitched audible sounds are created.

Thus, while it is generally recognized that plaque buildup is harmful and that techniques involving ultrasound can be used to remove plaque, many disadvantages result. For example, vibrating tip devices cannot be used in the home. These are primarily dentists' tools which require a skilled operator so as not to cause tooth damage or damage to surrounding gums, etc. Thus, it is a primary object of the present invention to provide a device and method for preventing excess plaque buildup, which device and method can be used by either a dentist or an individual at home.

All of the prior art techniques for removing plaque also involve some degree of discomfort. This is particularly noticeable with prior vibrating-tip devices and with the brute force of scaling or mechanical removal and abrasive particle applications. Thus, it is another object of the present invention to provide a tool and method for removal of plaque and for cleaning teeth which does not introduce discomfort due to mechanical scaling, vibration, or heat build-up.

In the prior art, there is also a device that utilizes a liquid jet which sprays dissolved sodium bicarbonate against the tooth to be cleaned. This device, due to the high pressure jet, acts somewhat similarly to a sand blaster and mechanically and chemically removes material from the teeth. A commercial device of this type is Prophy-Jet (Reg. trademark). A problem with using salt is that the solution can be easily swallowed during the cleaning operation, which means that the use of this technique should not be extended to persons having hypertension. Again, this device also cannot be used in the home. In addition, the device should not be used on sensitive teeth.

It is therefore another object of the present invention to provide an ultrasonic device and method for cleaning teeth which does not require the use of any type of abrasive particles or a high pressure jet.

It is a further object of this invention to provide a device and technique for improved cleaning of teeth, the device being sufficiently simple, safe and inexpensive that home use is possible.

It is another object of this invention to provide a device and technique for cleaning teeth which is neat and does not produce any bleeding during the cleaning operation.

It is still another object of the present invention to provide an improved device and method for cleaning teeth and removing plaque therefrom which can provide such cleaning in hard-to-reach areas, such as those between adjacent teeth.

It is a further object of this invention to provide an improved device and technique for cleaning teeth and removing plaque which utilizes a gentle stream of a liquid such as water, there being no harm to teeth or gums during the practice of this invention.

It is a further object of this invention to provide a device and technique for removing plaque and cleaning teeth, which can be conveniently adapted to home use by simply connecting the device to a water source, such as a faucet.

SUMMARY OF THE INVENTION

This dental cleaning device and technique utilizes an ultrasound wave preferably focused into a jet of liquid, preferrably a water jet, which is incident upon a tooth and causes cleaning of the tooth due to the ultrasonic energy. The liquid jet stream acts as a medium for carrying the sonic waves and also is used to carry away debris which is loosened by the sonic energy. The jet stream of water is extremely gentle and does not require abrasive particles or solid vibrating tips of the type used in the art. Further, it has been found that the cleaning action is excellent, there being plaque removal without the need for the type of mechanical abrasion produced by a vibrating tip or abrasive particles. The device includes a source of liquid (water), a transducer for creating sonic energy, means for coupling the sonic energy to a jet stream, and means for producing a small jet stream in which the sonic energy is contained. A pump and nozzle can be used to provide the liquid stream, while a control unit is used to provide electrical energy to the transducer for creating the ultrasound energy and for controlling the action of the pump to deliver the water to the nozzle. In an alternative embodiment, the water source can be a sink or faucet wherein a flexible tubing is used to carry the liquid to a housing connected to the nozzle. Depending on the water pressure, a pump may or may not be required.

Generally, the ultrasound energy has a frequency less than about 20 MHz, but frequencies above this can also be used. For coupling of low frequency sonic energy to the jet stream, an embodiment wherein a magnetostrictive transducer is located in the water supply can be used.

While it is preferrable to have the sonic energy continuously present in the jet stream, it is possible to use a pulsed type operation where the sonic energy is present in pulses in the jet stream.

These and other objects, features, and advantages will be apparent from the following more particular description of the preferred embodiments. Various configurations can be envisioned for carrying out this invention, which is based upon the discovery that a sonic wave contained in a liquid stream will provide excellent removal of plaque and teeth cleaning, without the necessity of a vibrating solid tip or the use of abrasive particles. Additionally, it has also been discovered that the jet stream can be extremely gentle so that no harm will occur to either teeth or gums even if the device is not used by a professional dentist.

DESCRIPTION OF THE PREFERRED EMBODIMENTS

Figure 1:
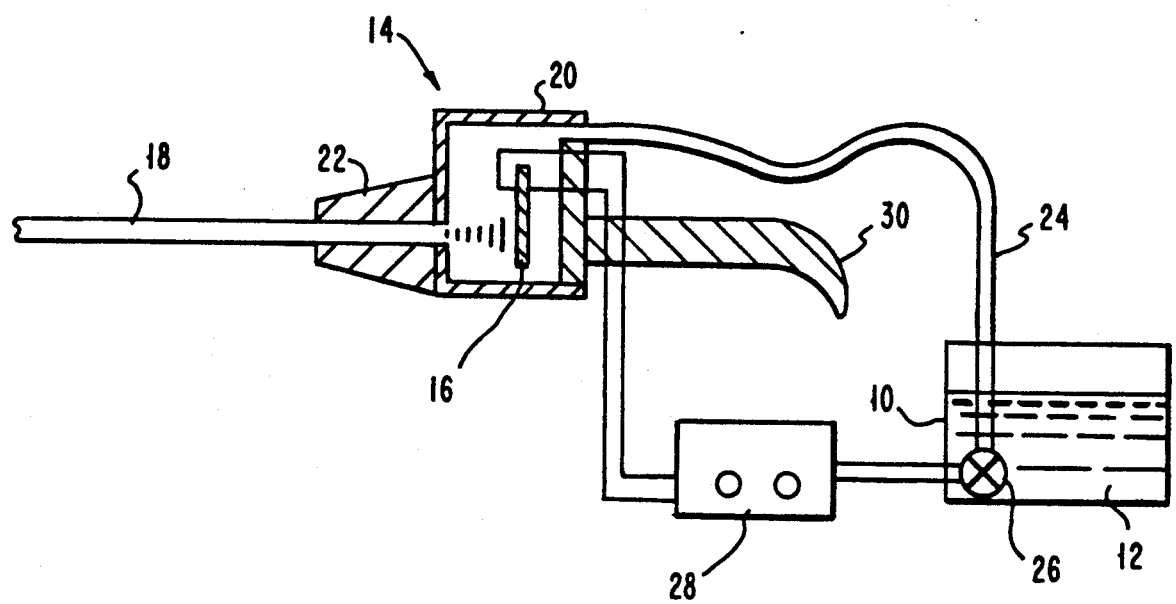
FIG. 1 is a schematic illustration of an apparatus suitable for carrying out the present invention wherein a transducer converts electrical energy into sonic energy which is then coupled into a liquid jet stream and directed at teeth to be cleaned of plaque.

FIG. 1 illustrates a suitable apparatus for carrying out the present invention, and broadly includes a reservoir 10 containing a liquid such as water 12, means 14 for creating a liquid stream, and a transducer means 16 for creating sonic energy which is coupled into the liquid jet stream 18 emerging from the device. Means 14 includes a housing 20 for containing the liquid 12 under pressure, a nozzle 22 from which a liquid stream exits, tubing 24 for delivering liquid from the reservoir 10 to the housing 20, and a pump 26 for moving the liquid under pressure to housing 20 and nozzle 22. A control unit 28 provides electrical energy to the transducer 16 to cause the ultrasonic wave to be generated and also provides power to the pump 26. The cleaning portion of the device is conveniently held by a handle 30.

In operation, the device is easily moved by hand using handle 30, which could also include a trigger to provide appropriate voltages to activate the control/drive unit 28 and pump 26. When electrical energy is provided to the transducer 16, sonic waves are created which are directly coupled into the liquid 12 contained in housing 20. Due to the pressure applied by pump 26, a sonified jet stream 18 of liquid will exit from nozzle 22. This stream will carry the sonic energy to the teeth to be cleaned, the sonic energy removing plaque therefrom. Any debris (such as particles) removed from the teeth will be carried away by the liquid.

Water or water-based solutions are the preferable liquids for carrying the sonic energy. The use of water (without any additives) has an advantage in that the nozzle won't be easily clogged by a non-dissolving additive or by an additive which comes out of solution. The acoustic mismatch between water and air is very large (approximately $10^4$), which means that most of the sonic energy coupled into the water stream will be contained by the stream. Additionally, the transducer 16 is designed to have very low mismatch with water so that a large percentage of the sonic energy is directly coupled into the water. As is known in the art, there is very little transmission of sonic energy from a transducer into air or a gas, and for this reason a liquid carrier is used. Of course, the liquid carrier also functions to remove debris and particles after cleaning. The frequency of the ultrasound energy extends over a wide range, the upper end of frequency being that at which it is impractical to fabricate a transducer for delivering high energy at high frequencies. Further, if the sonic frequency is too high (approximately 100 MHz), excess attenuation in water will occur. While the sonic wave frequency can be less than 5 MHz, a practical range is approximately 5–20 MHz. Generally, if the frequency is too low, it is difficult to couple sound energy into a finite sized stream. Using frequencies in the MHz range means that nonfocussing transducers can be used. Cleaning can occur at frequencies less than 1 MHz, though, as long as sufficient energy can be coupled into the stream.

The ultrasonic energy delivered by the sonic wave can also extend over a wide range, even up to an amount which would almost cause cavitation. For many fluids including water, cavitation will occur at energy levels greater than about $\frac{1}{2}$ kwatt per square centimeter, at low frequencies. In the frequency range of interest here cavitation occurs near 1 kW/cm$^2$.

Generally, it is desirable to have sonic energy in the jet stream 18 whenever cleaning is to occur. For that reason, continuous wave operation is preferrable. However, pulsed operation can be used in which the ultrasonic energy is produced in pulse form. Large power bursts for short time periods can be used for plaque removal if it is not possible to provide continuous wave ultrasonic energy or pulsed operation having a large duty cycle.

The diameter of the liquid jet stream 18 can be varied, localization of cleaning being dependent on the jet stream diameter. While this is not particularly important for all aspects of teeth cleaning, nozzles producing jet streams of about 0.5–3 mm have been very successful. The stream diameter is not critical, but streams that are too large deliver too much water (which can cause choking) and also place too much of a burden on the transducers in terms of the amount of sonic energy that is delivered, since adequate cleaning requires at least about 50–100 watts/cm$^2$, in the MHz frequency range. Larger stream diameters require very large total acoustic powers coupled into the stream, which is difficult to achieve.

As was noted previously, a very gentle liquid stream is provided so that no harm occurs to either teeth or gums. A nominal jet stream pressure is utilized which can be about ⅓ atmosphere. The purposes of the liquid stream are to act as a medium for the sonic energy and to remove debris so that as gentle a stream as possible is preferrable consistent with these functions.

The transducer element 16 and the control unit 28 are commercially available. A suitable transducer is one comprised of a piezoelectric element which radiates perpendicularly to the element to propagate a longitudinal sound wave in the liquid jet stream. The transducer and its electrical wires coupling electrical energy to it are generally sold as an encapsulated unit. A chamber holding the transducer and designed for coupling energy into a liquid such as water is readily fabricated with the transducer manufactured by Precision Acoustic Device Inc., located in Fremont, Calif. These transducers are well known and can receive up to several watts of electrical power to deliver 10-200 watts per square centimeter in a sound wave. The piezoelectric elements are generally lead-zirconium titanate. The transducer size is typically ½-2 cms in diameter. For focussing the sonic wave, spherical shells are commercially available from Valpey Fisher Co., Hopkinton, Mass. These spherical shells are designed by the manufacturer to couple the acoustic energy of the PZT transducer to water.

U.S. Pat. No. 4,507,969 describes a particular structure for directing an ultrasonic wave into a liquid jet, the apparatus of this reference being designed to improve the wave coupling performance of ultrasonic liquid jet probes. This is done by a particular design which enables the probe to discharge a uniform, stable liquid jet column.

Another structure describing the coupling of sonic waves from a PZT transducer to a liquid is R. J. von Gutfeld et al, Appl. Phys. Lett. 50 (7), P. 383, Feb. 16, 1987. In this reference, sonic energy is used to affect electroplating of gold and copper to provide deposits having improved morphology.

The control unit 28 is also commercially available and is generally provided for use with a particular transducer. For example, the PZT transducer described above can be obtained with an ultrasonic generator and control unit, and can also be ordered from Precision Acoustic Devices Inc.

Figure 2:
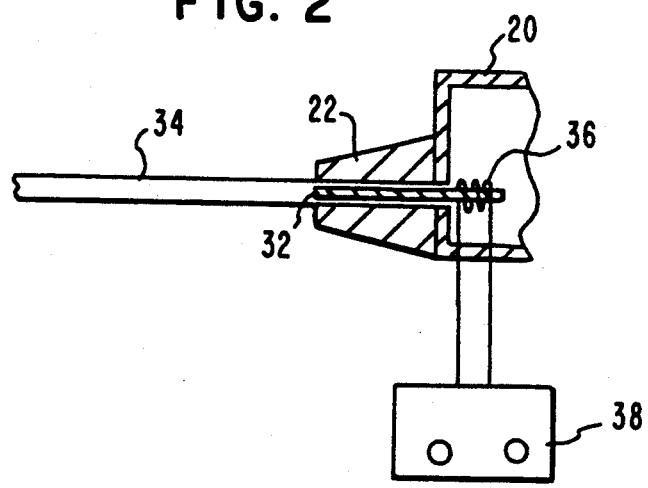
FIG. 2 schematically illustrates an arrangement using a magnetostrictive transducer for coupling lower frequency sonic energy into the liquid stream.

FIG. 2 illustrates an alternative embodiment in which high frequency sonic energy is directly coupled into a liquid stream. In this schematic illustration, a magnetostrictive rod 32 is located in the liquid stream 34 for directly coupling high frequency sonic energy to the stream. A coil 36, connected to driver 38, surrounds the magnetostrictive rod 32 for producing a magnetic field coupled to the rod. This would cause dimension changes of the rod to create vibrations, thereby coupling energy directly into the stream 34. For moderately high frequency applications (such as those in excess of about 50 kHz), this type of arrangement may provide better coupling of the sonic energy to the stream.

The following examples will illustrate the use of this invention to remove plaque from teeth.

EXAMPLE

Four freshly pulled teeth were examined and found to contain plaque. Sonic energy was applied via a water jet stream to remove the plaque. In these tests, the teeth are located in a chamber to catch and recirculate the water of the jet stream. The tooth is positioned about 1 cm. from the insonified stream. Approximately 1 watt average of electrical power was applied to the transducer, which was a PZT transducer Model No. 3-625-16 obtained from Precision Acoustic Devices Inc. Approximately 25% of the sonic energy produced was coupled into the water stream.

Prior to irradiating the teeth with sonic energy, a disclosing solution was applied to the teeth. This type of solution contains a red dye which sticks to the teeth if plaque is present. Various teeth were tested using a jet having sonic energy therein, as well as water jets which did not contain sonic energy.

The teeth exposed to a water jet containing sonic energy were treated for up to about 4 minutes total time per tooth. The frequency of the ultrasound was 9.6 MHz. Upon treatment with a water jet containing ultrasound energy, the disclosing solution changed color from red to very light pink. For those teeth exposed to a water jet without sonic energy, only very little change in color was seen.

After exposure of the teeth to the water jet, the teeth were examined and a scaling tool was then used. It was found that, for those teeth which were exposed to the water jet without sonic energy, there was essentially no decrease in plaque content. For those teeth to which ultrasound energy was applied, the teeth were essentially plaque-free.

In these tests, the nozzle opening was about 1 mm, but openings having different diameters are suitable. For example, nozzle openings less than ½ mm can also be used.

As noted previously, alternative embodiments can be envisioned. For example, the water reservoir can be a sink or faucet of the type provided in the home. If other applications are foreseen, such as drilling bone matter or flushing out kidney stones, or teeth drilling, more powerful transducers can be used to couple sonic waves of high energy into the jet stream. Further, operation can be in a pulsed mode, wherein higher energy sonic pulses can be produced without damage to the transducers.

It will be understood by those of skill in the art that the amount of sonic energy transmitted in the jet stream to the tooth will depend on how effectively sonic energy is coupled into the stream, as well as by losses of sonic energy to the housing 20 and nozzle 22. For this reason, the materials comprising housing 20 and nozzle 22 are chosen to be those having large acoustic mismatches with water. An example is a thin steel bellows used for the nozzle and the housing, since the acoustic impedance mismatch between water and steel is quite large. In contrast, a nozzle and housing material such as plastic would not work as well since the water-plastic acoustic mismatch is not as great as that between water and steel.

While the invention has been described with respect to particular embodiments thereof, it will be appreciated by those of skill in the art that variations can be made thereto without departing from the spirit and scope of the present invention. For example, other liquids may also couple sonic energy well, although water is preferred because it is not harmful to health and contains sonic energy well. Further, the exact type of transducer and the techniques for coupling sonic energy to the jet stream can be varied while still utilizing the concept of a liquid stream containing ultrasonic energy to remove plaque from teeth. Commerically available transducers are designed for coupling into different media, and can be obtained with acoustic lenses for optimal coupling. Most of these transducers are designed to couple sound energy into a liquid, particularly water.

Having thus described our invention what we claim as new and desire to secure as Letters Patent, is:

1. A method for removing plaque from a tooth including the steps of focussing an ultrasound sonic wave in a liquid stream to form a sonified liquid stream, said sonic wave having a frequency in the range of about 1–100 MHz and directing said sonified liquid stream at said tooth, the energy of the focussed sonic wave in said stream being sufficient to remove plaque from said tooth, said liquid stream having a pressure less than that which would cause damage to gums surrounding said tooth.

2. The method of claim 1, where said liquid is water.

3. The method of claim 1, where said stream has a diameter in the range of several millimeters and less.

4. The method of claim 1, where said sonic wave is a continuous wave.

5. The method of claim 1, where said sonic wave is a pulsed wave.

6. A method for removing plaque from teeth including the steps of:

delivering water through a tubing from a water source to a chamber containing a transducer for producing sound waves in the MHz frequency range, applying electromagnetic energy to said transducer to produce a focussed sonic wave coupled to water in said chamber, expelling a stream of water having focussed sonic energy therein from said chamber to form a sonified jet stream of water, said stream of water having a pressure less than 10 psi, directing said focussed sonified jet stream to said teeth, said focussed sonic wave cleaning said teeth by removing plaque therefrom.

7. The method of claim 6, wherein said stream has a diameter when leaving said chamber of less than several millimeters.

8. The method of claim 6, including the additional step of scanning said sonified stream across said teeth.

9. The method of claim 6, where said sonic wave has a frequency in the range of about 1 MHz to about 25 MHz.

10. The method of claim 6, where said sonic wave is a continuous wave.

11. The method of claim 6, where said sonic wave is a pulsed or gated wave.

12. The method of claim 6, where said stream has a diameter in the range of several millimeters and less, said sonic wave has a frequency less than about 25 MHz, and said sonic wave is a continous wave.

13. An apparatus for removing plaque from teeth, including:

sonic means for producing a focussed sonic wave in a liquid, said sonic wave having a frequency in the range of about 1–100 MHz means for delivering a sonified liquid stream to a tooth to be cleaned, the focussed sonic energy in said stream being sufficient to remove plaque from said tooth, said liquid stream having a pressure less than which causes damage to gums surrounding said teeth.

14. The apparatus of claim 13, where said focussed sonic wave is a continuous wave.

15. The apparatus of claim 13, where said focussed sonic wave has a frequency less than 100 MHz.

16. The apparatus of claim 13, where said liquid is water.

17. The apparatus of claim 13, including tubing means and a pump for delivering said liquid from a reservoir to said sonic means.

18. The apparatus of claim 17, where said reservoir is a sink.

19. The apparatus of claim 19, where said liquid is water and the frequency of said focussed sonic wave is about 1 MHz–25 MHz.

20. The apparatus of claim 13, where said means for delivering includes a chamber having said liquid therein and a nozzle through which said sonified stream exits.

21. The apparatus of claim 20, where the inner diameter of said nozzle is in the millimeter or less range.

22. The apparatus of claim 13, where said focussed sonic means includes a transducer for producing a sonic wave in response to electromagnetic energy applied thereto.

23. The apparatus of claim 22, including an electrical means for providing electro-magnetic energy to said transducer, a chamber for containing said liquid and said transducer, and a pump for bringing said liquid to said chamber.

24. The apparatus of claim 13, including tubing means connected to a faucet for delivering said liquid to said sonic means.

25. An apparatus for cleaning teeth comprising:

a chamber containing a liquid, a transducer for producing focussed sonic energy of about 1–100 MHz frequency in said liquid when electromagnetic energy is applied thereto, means for providing electromagnetic energy to said transducer, a nozzle through which said liquid can exit as a sonified jet stream having a pressure less than about 10 psi, and means for directing said sonified jet stream to said teeth, the focussed sonic energy in said stream being sufficient to clean said teeth.

26. The apparatus of claim 25, where said liquid is water.

27. The apparatus of claim 25, where said focussed sonic energy is pulsed.

28. A method for removing plaque from a tooth including the steps of focussing an ultrasound sonic wave in a liquid stream to form a sonified liquid stream, said sonic wave having a frequency in the range of about 2–25 MHz and directing said sonified liquid stream at said tooth, the energy of the focussed sonic wave in said stream being sufficient to remove plaque from said tooth.

* * * * *